United States Patent
Sutoris et al.

(10) Patent No.: US 6,835,288 B1
(45) Date of Patent: Dec. 28, 2004

(54) METHOD FOR PREVENTING UNDESIRED POLYMERIZATION IN A MIXTURE OF SUBSTANCES CONTAINING ETHYLENICALLY UNSATURATED COMPOUNDS

(75) Inventors: Heinz Friedrich Sutoris, Worms (DE); Konrad Mitulla, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 421 days.

(21) Appl. No.: 09/926,743

(22) PCT Filed: Jun. 9, 2000

(86) PCT No.: PCT/EP00/05360

§ 371 (c)(1),
(2), (4) Date: Dec. 11, 2001

(87) PCT Pub. No.: WO00/76943

PCT Pub. Date: Dec. 21, 2000

(30) Foreign Application Priority Data

Jun. 11, 1999 (DE) .......................................... 199 26 758

(51) Int. Cl.$^7$ ............................. C07C 7/05; C07B 63/04
(52) U.S. Cl. ..................... 203/3; 203/8; 203/9; 203/71; 203/DIG. 18; 585/3; 585/4; 585/5; 204/158.21
(58) Field of Search ............................... 203/2, 3, 8, 9, 203/DIG. 18, 71; 562/600; 585/3, 4, 5, 860; 204/158.21

(56) References Cited

U.S. PATENT DOCUMENTS 5,254,760 A  10/1993  Winter et al.
5,368,699 A  * 11/1994  Rhiel et al. ..................... 203/2
5,545,782 A   8/1996  Winter et al.
5,545,786 A   8/1996  Winter et al.
6,268,441 B1 *  7/2001  Lynch et al. ................... 526/74
6,300,513 B2 * 10/2001  Sakamoto et al. ............. 560/4
6,664,418 B1 * 12/2003  Sakamoto et al. ......... 562/598

FOREIGN PATENT DOCUMENTS

| DE | 19622498 | 11/2000 |
| DE | 19651307 | 3/2001 |
| GB | 992 548 | 5/1965 |
| JP | 1-165534 | 6/1989 |
| SU | 1027150 | 7/1983 |
| SU | 1 139 722 | 2/1985 |
| SU | 1139722 | 2/1985 |
| SU | 1558888 | 4/1990 |
| SU | 1 558 888 | 4/1990 |
| WO | 96 16921 | 6/1996 |

\* cited by examiner

*Primary Examiner*—Virginia Manoharan
(74) *Attorney, Agent, or Firm*—Oblon, Spivak, McClelland, Maier & Neustadt, P.C.

(57) ABSTRACT

A process for preventing undesired polymerization is conducted by maintaining an effective concentration of a stabilizer which comprises N-oxyl radicals in a mixture containing ethylenically unsaturated compounds, wherein (i) an electronic signal which correlates with the concentration of the N-oxyl radicals in the mixture is obtained periodically or continuously, (ii) the electronic signal is compared with a reference value, and (iii) addition of a stabilizer to the mixture is controlled according to the comparison (ii).

Figure 1:
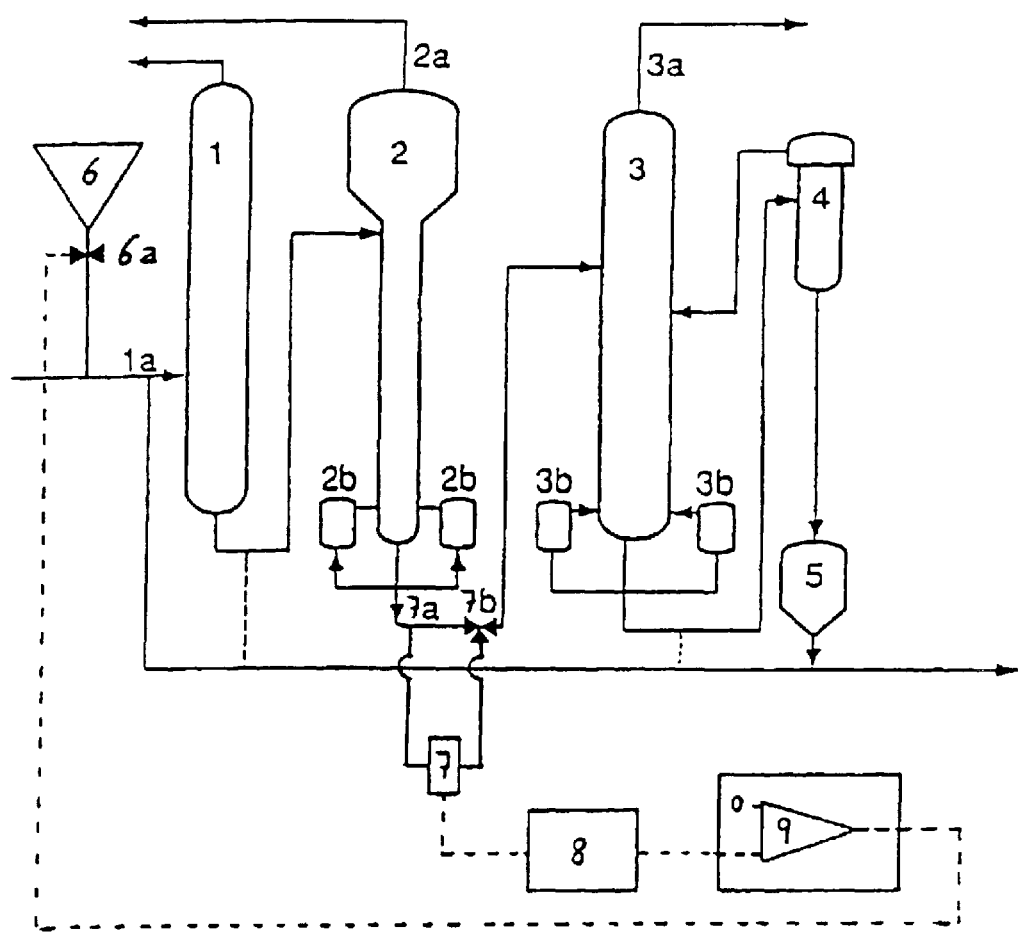

The signal is preferably obtained by ESR measurement. The process permits efficient use of the stabilizer.

21 Claims, 1 Drawing Sheet

METHOD FOR PREVENTING UNDESIRED POLYMERIZATION IN A MIXTURE OF SUBSTANCES CONTAINING ETHYLENICALLY UNSATURATED COMPOUNDS

BACKGROUND OF THE INVENTION

1. Field of the Invention

The present invention relates to a process for preventing undesired polymerization in a mixture containing ethylenically unsaturated compounds, in particular in the isolation of ethylenically unsaturated compounds from a mixture containing them by distillation.

2. Description of the Background

It is known that many unsaturated compounds tend to undergo generally free radical polymerization when the temperature is increased. For example, vinylaromatic compounds, such as styrene or α-methylstyrene, have to be stabilized with suitable compounds to prevent premature polymerization in the purification of the industrially obtained crude products by distillation. Usually, stabilizers or polymerization inhibitors are added to the crude products to be distilled, before or during the purification step. In spite of this measure, a certain amount of oligomers or polymers is obtained. In specific cases, especially when operating faults occur, complete polymerization of the monomers present or of the monomer mixture can take place during the purification or distillation. Costs are incurred as a result, owing to the extensive cleaning effort and loss of production.

The ethylenically unsaturated compounds obtained in pure form must furthermore be protected from undesired premature polymerization during storage or handling, for example during derivatizing.

USSR patents SU-1027150, SU-1558888 and SU-1139722 describe the stabilization of styrene by using nitroxyl or bisnitroxyl compounds.

WO-96/16921 discloses mixtures of vinylaromatic compounds with sterically hindered nitroxyl compounds, which are activated by traces of oxygen.

JP Hei 1-165534 discloses piperidyloxy derivatives as polymerization inhibitors for styrene.

U.S. Pat. No. 5,254,760 and DE-19622498 describe mixtures of nitroxyl and nitro compounds for stabilizing vinylaromatic compounds during purification or distillation.

DE 19651307 describes mixtures which contain vinyl-containing compounds, such as styrene, and a mixture of an N-oxyl compound and an iron compound, which mixture inhibits premature polymerization. The mixtures are effectively stabilized against premature polymerization during purification or distillation.

To ensure the sufficient stabilization, the nitroxyl radicals must be present in a specific minimum concentration in the mixtures containing ethylenically unsaturated compounds. As a result of scavenging reactions with spontaneously forming radicals, a certain amount of nitroxyl radicals is continuously consumed. The rate of consumption depends on external variables, such as the temperature, the presence of free radical initiators, the admittance of oxygen, etc. These variables can sometimes fluctuate unpredictably. To ensure sufficient stabilization even under unfavorable conditions, the nitroxyl radical must therefore be added in a more or less large excess to the mixtures to be stabilized. Since nitroxyl radicals are comparatively expensive polymerization inhibitors, the required amount of nitroxyl radicals for stabilization during purification and/or handling constitutes a cost factor which is not negligible. It is therefore desirable to keep the excess in the metering of nitroxyl radicals as small as possible or to avoid such excess.

SUMMARY OF THE INVENTION

It is an object of the present invention to provide a process for preventing undesired polymerization in a mixture containing ethylenically unsaturated compounds, in particular in the isolation of ethylenically unsaturated compounds by distillation from a mixture containing them, in which process the stabilizer is used very efficiently.

We have found that this object is achieved if the concentration of the N-oxyl radicals having at least one unpaired electron can be electronically determined in a comparatively simple manner so that an addition of stabilizer can be effectively controlled.

The present invention accordingly relates to a process for preventing undesired polymerization in a mixture containing ethylenically unsaturated compounds by maintaining an effective concentration of a stabilizer system which comprises N-oxyl radicals, wherein (i) an electronic signal which correlates with the concentration of the N-oxyl radicals in the mixture is obtained periodically or continuously, (ii) the electronic signal is compared with a reference value and (iii) an addition of stabilizer system to the mixture is controlled according to the comparison.

The present invention also relates to a process for isolating ethylenically unsaturated compounds from a mixture containing them by distillation of the mixture while maintaining an effective concentration of a stabilizer system in the mixture which comprises free N-oxyl radicals, wherein (i) an electronic signal which correlates with the concentration of the N-oxyl radicals in the mixture is obtained periodically or continuously, (ii) the electronic signal is compared with a reference value and (iii) an addition of the stabilizer system to the mixture is controlled according to the comparison.

DETAILED DESCRIPTION OF THE PREFERRED EMBODIMENTS

In a preferred process, the distillation is carried out in a cascade of a plurality of distillation columns, wherein a high boiler fraction containing the stabilizer system accumulates in the bottom of at least one distillation column and a part-stream of the high boiler fraction is removed and is mixed with the feed of an upstream column.

The concentration of the N-oxyl radicals in the mixture to be stabilized is preferably at least 0.1 ppm, in particular from 1 to 500 ppm, particularly preferably from 5 to 150 ppm, based on ethylenically unsaturated compound.

N-Oxyl radicals used according to the invention are characterized by at least one unpaired electron. They can therefore readily be detected, for example, by ESR (electron spin resonance) or EPR (electron paramagnetic resonance) spectroscopy. These spectroscopy methods are based on the fact that the electron has a spin s of ½. If such a particle is brought into homogeneous constant magnetic field $H_0$, the field exerts on the particle a force which attempts to turn this magnetic moment and hence its spin vector in the field direction. Under the influence of this force, the electron performs a precession movement about the axis of the external field, which is usually referred to as Larmor precession. If a second high frequency magnetic field $H_1$ is added perpendicular to the constant field $H_0$, resonance occurs if the frequency of the $H_1$ field v is equal to the frequency of the Larmor precession $V_L$. The incidence of an electromagnetic wave of suitable frequency v results in magnetic resonance absorption, the magnitude of which can be measured.

Accordingly, the electronic signal is preferably obtained by exposing the mixture or a portion thereof to a magnetic field and simultaneously applying an alternating electromagnetic field, the resonance caused by the N-oxyl radicals being detected.

Usually, the constant magnetic field $H_0$ has a constant magnitude in the region of about 0.34 Tesla. The frequency of the high-frequency magnetic field $H_1$ is varied continuously until resonance occurs. At a field strength of 0.34 Tesla, the absorption of the N-oxyl radicals is in the microwave range ($v\sim10^{10}$ Hz). Since, with the novel use of N-oxyl radicals, the frequency at which resonance is to be expected is known, it is possible to dispense with expensive apparatuses for varying the frequency of the magnetic field $H_1$. It is therefore possible to effect exposure to a fixed frequency $V_f$ which is at or close to the resonance maximum of N-oxyl radicals used, for a given constant magnetic field $H_0$. This considerably reduces the cost of the apparatus for carrying out the novel process.

In a practical embodiment, for example, a flow-through measuring cell with an integrated magnet, resonator and microwave bridge is used. The flow-through measuring cell is arranged, for example, at a suitable point in a pipeline through which the mixture to be stabilized flows. Often, it is desirable to keep the sample free from flow during the ESR measurement. In this case, the measuring cell is advantageously arranged in a bypass line which is connected, for example via a T-connector and a directional valve, to the pipeline carrying the mixture. By switching the valve, the mixture is briefly passed through the bypass line until the measuring cell is full. The bypass line is then disconnected from the pipeline by switching the valve again. In the measuring cell, the ESR spectrum is then measured on the stationary sample. After the measurement, the valve is switched again, with the result that the measuring cell is rinsed and is filled with fresh mixture. The operations of rinsing, disconnecting and measuring are repeated periodically. Preferably, they are automated. Suitable EPR/ESR spectrometers having flow-through measuring cells are sold, for example, by Magnettech GmbH, Berlin, under the name "Miniscope".

The initially detected resonance signal can be converted into a more expedient electronic signal, preferably using a suitably programmed data processor, for example by integration, filtration and/or other operations. The electronic signal obtained correlates with the concentration of the N-oxyl radicals in the mixture. It may be a DC signal of variable voltage or an AC signal of variable amplitude and/or frequency. Other signal shapes are possible. Suitable signal shapes are familiar to persons skilled in the art of measurement and control technology. The electronic signal may be proportional to the concentration of the N-oxyl radicals but may also correlate with the concentration according to any other mathematical function which leads to the actual concentration of the N-oxyl radical. The electronic signal is then compared with a reference value. This comparison is preferably performed automatically by a comparator suitable for this purpose. Comparison can be performed, for example, by calculating a signal which is the difference between the electronic signal and the reference value. A person skilled in the art in the area of measurement and control technology can readily provide a suitable arrangement and circuit for carrying out the comparison.

The reference value may be a freely selectable, constant value which corresponds, for example, to an empirically determined, effective concentration of N-oxyl radicals. However, it is also possible for the reference value in turn to be dependent on further measured variables. The further measured variables are preferably likewise measured periodically or continuously and provided in the form of an electronic signal. Such further measured variables include, for example, the temperature of the mixture, the ambient temperature, the redox potential of the mixture, the near infrared (NIR) transmission or absorption, the turbidity, the viscosity, the density or the refractive index of the mixture. Thus, the reference value can be adapted to all cases in which a relatively large amount of stabilizers is temporarily required for preventing an undesired polymerization, for example in the event of a temperature increase.

The addition of the stabilizer system to the mixture is controlled according to the comparison of the electronic signal with the reference value. The addition of the stabilizer system is preferably effected by means of an automatic metering unit with which preselectable amounts, for example of a solution, described below, of the stabilizer system in a suitable solvent, can be added. Metering pumps, micrometering pumps, differential metering pumps, for example having twin screws as a conveying element, etc. are suitable.

In many cases, it is advantageous to provide continuous metering of the stabilizer system into the mixture, which metering is modulated according to the comparison.

If it is found in the comparison that the concentration of N-oxyl radicals which corresponds to the electronic signal determined is lower than that corresponding to the reference value, measures are initiated to increase the concentration of the N-oxyl radicals, for example addition of stabilizer system to the mixture or an increase in the rate of addition. If on the other hand, the comparison reveals that the concentration corresponding to the electronic signal determined is higher than that corresponding to the reference value, the addition of stabilizer system is suppressed or the rate of addition is decreased.

The addition of the stabilizer system is preferably controlled in such a way that the concentration of the N-oxyl radicals in the mixture is at least 0.1 ppm, in particular from 1 to 1000 ppm, particularly preferably from 1 to 500 ppm, preferably from 5 to 150 ppm.

In the novel distillation process the stabilizer system is preferably added to the bottom of the distillation or to at least one bottom of an arrangement of a plurality of distillation apparatuses, such as distillation columns, or is mixed with the feed to the distillation apparatus.

The mixtures in the context of the invention may be pure ethylenically unsaturated compounds or any homogeneous or heterogeneous mixtures which contain ethylenically unsaturated compounds in a concentration such that a polymerization, usually a free radical polymerization, can take place.

Ethylenically unsaturated compounds within the scope of the invention are in particular α,β-ethylenically unsaturated $C_3$–$C_6$-monocarboxylic acids or $C_4$–$C_6$-dicarboxylic acids, such as acrylic acid, methacrylic acid, maleic acid, fumaric acid and itaconic acid, esters of α,β-ethylenically unsaturated $C_3$–$C_6$-monocarboxylic acids or $C_4$–$C_6$-dicarboxylic acids, such as methyl (meth)acrylate, ethyl (meth)acrylate, n-butyl (meth)acrylate, isobutyl (meth)acrylate, tert-butyl (meth)acrylate and 2-ethylhexyl (meth)acrylate, vinylaromatic compounds, such as styrene, α-methylstyrene, o-chlorostyrene, vinyltoluenes, divinylbenzene, nitrostyrene and styrenesulfonic acid, heteroaromatic vinyl compounds, such as vinylpyridine, vinyl esters of $C_1$–$C_{18}$-monocarboxylic acids or dicarboxylic acids, such as vinyl acetate, vinyl propionate, vinyl n-butyrate, vinyl laurate and vinyl stearate, linear or branched 1-olefins or cyclic olefins, e.g. propene, butene, isobutene, pentene, cyclopentene, hexene, cyclohexene, octene, 2,4,4-trimethyl-1-pentene, if desired as a mixture with 2,4,4-trimethyl-2-pentene, $C_8$–$C_{10}$-olefin, 1-dodecene, $C_{12}$–$C_{14}$-olefin, octadecene, 1-eicosene and $C_{20}$–$C_{24}$-olefin, acrylonitrile and methacrylonitrile, vinyl and allyl alkyl ethers having 1–40 carbon atoms in the alkyl radical, it being possible for the alkyl radical to carry further substituents, such as hydroxyl, amino or dialkylamino or one or more alkoxylate groups, e.g. methyl vinyl ether, ethyl vinyl ether, propyl vinyl ether, isobutyl vinyl ether, 2-ethylhexyl vinyl ether, vinyl cyclohexyl ether, vinyl 4-hydroxybutyl ether, decyl vinyl ether, dodecyl vinyl ether, octadecyl vinyl ether, 2-(diethylamino)ethyl vinyl ether, 2-(di-n-butylamino) ethyl vinyl ether, methyldiglycol vinyl ether and the corresponding allyl ethers, or mixtures thereof, acrylamides and alkyl-substituted acrylamides, e.g. acrylamide, methacrylamide, N-tert-butylacrylamide and N-methyl (meth)acrylamide, vinyl halides and vinylidene halides, such as vinyl chloride, vinylidene chloride, vinyl fluoride and vinyl bromide, polyethylenically unsaturated compounds, such as butadiene and chloroprene, sulfo-containing monomers, such as allylsulfonic acid, methallylsulfonic acid, vinylsulfonic acid, allyloxybenzenesulfonic acid, 2-acrylamido-2-methylpropanesulfonic acid, the alkali metal or ammonium salts thereof, sulfopropyl acrylate and sulfopropyl methacrylate, $C_1$–$C_4$-hydroxyalkyl esters of ethylenically unsaturated $C_3$–$C_6$-monocarboxylic acids or $C_4$–$C_6$-dicarboxylic acids, in particular of acrylic acid, methacrylic acid or maleic acid, or the derivatives alkoxylated with 2–50 mol of ethylene oxide, propylene oxide, butylene oxide or mixtures thereof, or esters of said acids with $C_1$–$C_{18}$-alcohols alkoxylated with 2–50 mol of ethylene oxide, propylene oxide, butylene oxide or mixtures thereof, e.g. hydroxyethyl (meth)acrylate, hydroxypropyl (meth)acrylate, 1,4-butanediol monoacrylate, ethyldiglycol acrylate, methylpolyglycol acrylate (11 EO), methacrylates of $C_{13}/C_{15}$-oxo alcohols reacted with 3, 5, 7, 10 or 30 mol of ethylene oxide, or mixtures thereof, vinylphosphonic acid, dimethyl vinylphosphonate and other phosphorus-containing monomers, alkylaminoalkyl (meth)acrylates or alkylaminoalkyl (meth)acrylamides or their quaternization products, e.g. 2-(N,N-dimethylamino)ethyl (meth)acrylate, 3-(N,N-dimethylamino)propyl (meth)acrylate, 2-(N,N-triethylammonium)ethyl (meth)acrylate chloride, 2-dimethylaminoethyl (meth)acrylamide, 3-dimethylaminopropyl(meth)acrylamide and 3-trimethylammoniumpropyl(meth)acrylamide chloride, allyl esters of $C_1$–$C_{30}$-monocarboxylic acids, N-vinyl compounds, such as N-vinylformamide, N-vinyl-N-methylformamide, N-vinylpyrrolidone, N-vinylimidazole, 1-vinyl-2-methylimidazole, 1-vinyl-2-methylimidazoline, N-vinylcaprolactam and vinylcarbazole, diallyldimethylammonium chloride, acrolein and methacrolein, monomers containing 1,3-diketo groups, e.g. acetoacetoxyethyl (meth)acrylate or diacetoneacrylamide, monomers containing urea groups, such as ureidoethyl (meth)acrylate, acrylamidoglycolic acid, methacrylamidoglycolate methyl ether, silyl-containing monomers, e.g. trimethoxysilylpropyl (meth)acrylate, glycidyl-containing monomers, e.g. glycidyl (meth) acrylate.

The invention is particularly suitable for preventing undesired polymerization of mixtures containing vinylaromatic compounds, in particular during their distillation.

Typical mixtures which contain one or more of the above-mentioned ethylenically unsaturated compounds are, for example, the crude mixtures which are initially obtained in the preparation of the unsaturated compounds from suitable precursor compounds and from which the pure ethylenically unsaturated compounds are isolated by distillation or other working-up methods. A preferred example is crude styrene, i.e. a crude mixture which is obtained in the preparation of styrene from ethylbenzene and contains minor amounts of toluene, benzene, cumene and/or α-methylstyrene in addition to styrene and ethylbenzene. Furthermore, crude styrene typically contains up to 3, for example from 0.5 to 1.2%, by eight, based on styrene, of components having a higher boiling point than styrene (i.e. higher boilers), such as stilbenes, styrene oligomers and styrene polymers as well as diphenylethane and 2-phenylnaphthalene. Typical mixtures have, for example, the following composition: 1% of benzene, 2% of toluene, 40% of ethylbenzene, 56% of styrene and 1% of higher boilers.

The esterification mixtures which were obtained in the esterification of acrylic acid or methacrylic acid with monohydric or polyhydric alcohols and from which the pure alkyl (meth)acrylate can be isolated by distillation are a further typical example.

Another typical mixture is a steam cracker fraction having a high content of α-olefins.

A further area of use of the invention is the chemical conversion of ethylenically unsaturated compounds in reaction in which the C—C double bond is not involved, for example the quaternization of amino-containing ethylenically unsaturated compounds.

For the purposes of the invention, the stabilizer system which comprises N-oxyl radicals is used. The N-oxyl radicals are stable free radicals which are sometimes also referred to as persistent radicals. They have one or more unpaired electrons. As a rule, they can be prepared as a pure substance and have a shelflife of years without decomposition. They themselves are not capable of initiating a free radical polymerization. They readily scavenge organic radicals which are spontaneously formed from ethylenically unsaturated compounds, for example during distillation. As a rule, the N-oxyl radicals are sterically hindered, i.e. they are derived from a secondary amine whose hydrogen atoms in α-position to the nitrogen atom which carries the oxyl group are all substituted, for example by alkyl groups.

In addition to the N-oxyl radicals, the stabilizer system may contain further components, such as the polymerization inhibitors or activators described below.

Suitable N-oxyls have, for example, the following structures

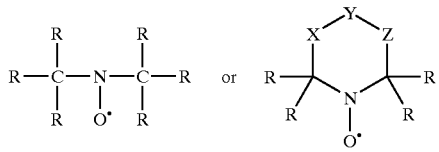

where R are identical or different alkyl, cycloalkyl, aralkyl or aryl radicals of up to 24 carbon atoms, it being possible for geminal R radicals also to be linked in pairs to form a ring system, and X, Y and Z, independently of one another, are CR'$_2$, CR'OH, CR'(COOH), O, S, CO or a chemical bond, with the proviso that not more than one X, Y or Z radical is O or S and not more than one X, Y or Z radical is a chemical bond. R' is hydrogen or an alkyl, cycloalkyl, aralkyl or aryl radical of up to 24 carbon atoms. For example, R is a $C_1$–$C_{20}$-alkyl radical, in particular $C_1$–$C_8$-alkyl radical, a $C_5$ or $C_6$-cycloalkyl radical, a benzyl radical or a phenyl radical. X-Y-Z is, for example, —(CH$_2$)$_2$—, —(CH$_2$)$_3$—, —CH$_2$—CH(OH)—CH$_2$—, —CH$_2$—CO—O— or —CH$_2$—O—.

Furthermore, N-oxyl compounds having aromatic substituents, such as the following structures

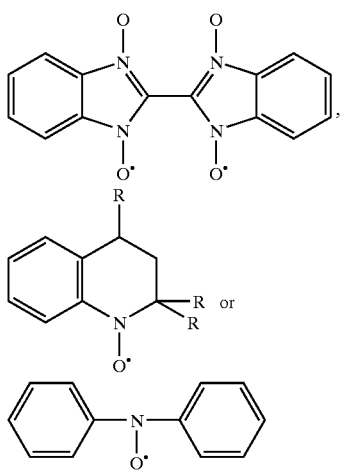

where the aromatic rings each furthermore carry 1 to 3 inert substituents, e.g. $C_1$–$C_4$-alkyl, $C_1$–$C_4$-alkoxy, ester, amide or cyano, are also suitable.

Preferably used N-oxyl radicals are those which are derived from cyclic amines, for example from piperidine or pyrrolidine compounds which may contain a further heteroatom, such as nitrogen, oxygen or sulfur, in the ring, this heteroatom not being in the neighboring position to the amine nitrogen. The steric hindrance is provided by substituents in both neighboring positions to the amine nitrogen, suitable substituents being hydrocarbon radicals, which replace all 4 hydrogen atoms of the α-CH$_2$ groups. Examples of substituents are phenyl, $C_3$–$C_6$-cycloalkyl, benzyl and in particular $C_1$–$C_6$-alkyl, it also being possible for the alkyl radicals bonded to the same α carbon atom to be linked to one another to form a 5- or 6-membered ring. Preferably used N-oxyls are sterically hindered amine derivatives of 2,2,6,6-tetraalkylpiperidine.

Preferred N-oxyl compounds are those of the formula (II) or (II')

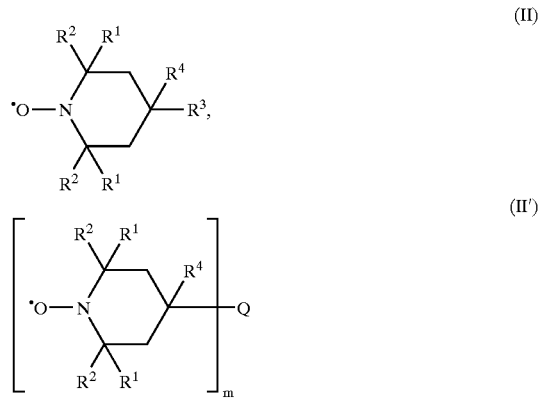

where $R^1$ and $R^2$ independently of one another, are each $C_1$–$C_4$-alkyl or phenyl or $R^1$ and $R^2$, together with the carbon atom to which they are bonded, form a 5- or a 6-membered, unsubstituted or substituted, saturated hydrocarbon ring which may contain 1 or 2 heteroatoms, selected from O, S and N, and 1 or 2 keto groups, $R^3$ is hydrogen, hydroxyl, amino, SO$_3$H, SO$_3$M, PO$_3$H$_2$, PO$_3$HM, PO$_3$M$_2$, an organosilicon radical or a monovalent organic radical bonded via carbon, oxygen or nitrogen and preferably of 1 to 36 atoms, M being an alkali metal, preferably Li, Na or K, $R^4$ is hydrogen, $C_1$–$C_{12}$-alkyl or $C_1$–$C_{12}$-alkoxy or $R^3$ and $R^4$ together are oxygen or $R^3$ and $R^4$, together with the carbon atom to which they are bonded, form a 5- or 6-membered, unsubstituted or substituted, saturated ring which may contain 1 or 2 heteroatoms, selected from O, S and N, and 1 or 2 keto groups, Q is a m-valent organic radical bonded via carbon, oxygen or nitrogen and preferably of 2 to 10,000, in particular 4 to 2000, atoms and m is from 2 to 100, preferably 2 or 3.

$R^1$ and $R^2$ may be $C_1$–$C_4$-alkyl, such as methyl, ethyl, n-propyl, isopropyl, n-butyl, isobutyl, sec-butyl or tert-butyl, or together they may form a tetra- or pentamethylene group. $R^1$ and $R^2$ are each preferably methyl.

Examples of suitable radicals $R^4$ are hydrogen, the abovementioned $C_1$–$C_4$-alkyl groups and pentyl, sec-pentyl, tert-pentyl, neopentyl, 2,3-dimethylbut-2-yl, hexyl, 2-methylpentyl, heptyl, 2-methylhexyl, 2-ethylhexyl, octyl, isooctyl, 2-ethylhexyl, nonyl, 2-methylnonyl, isononyl, 2-methyloctyl, decyl, isodecyl, 2-methylnonyl, undecyl, isoundecyl, dodecyl and isododecyl.

Preferred radicals $R^3$ are hydrogen, $C_1$–$C_{20}$-alkyl, such as methyl, ethyl, n-propyl, isopropyl, n-butyl, isobutyl and pentyl, hydroxyl, $C_2$–$C_{20}$-alkoxy, such as methoxy, ethoxy, propoxy and tert-butoxy,

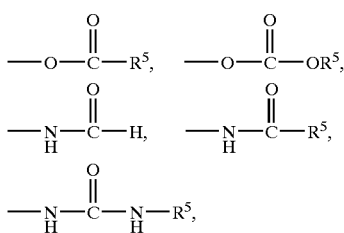

where $R^5$ is $C_1$–$C_{12}$-alkyl, $C_6$–$C_{12}$-aryl or $C_7$–$C_{14}$-aralkyl, and organosilicon radicals of the formula

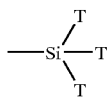

where the groups T may be identical or different and are $C_1$–$C_{12}$-alkyl or phenyl.

Examples of such organosilicon radicals are —Si(CH$_3$)$_3$ and —Si(C$_2$H$_5$)$_3$.

$R^3$ and $R^4$, together with the carbon atom to which they are bonded may be, for example

Preferred radicals Q are, for example, the following radicals

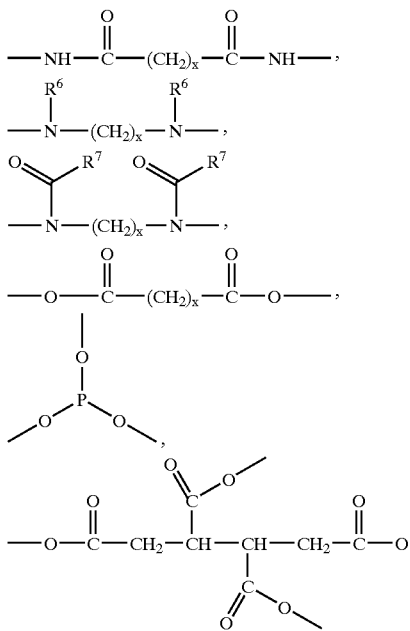

where
$R^6$ is $C_1$–$C_{12}$-alkyl,
$R^7$ is hydrogen or $C_1$–$C_{18}$-alkyl, and
x is from 1 to 12.

Further suitable N-oxyls are also oligomeric or polymeric compounds which have a polysiloxane as the polymer main chain and are substituted in the side chain by N-oxyl groups which are derived from 2,2,6,6-tetraalkylpiperidine. The preferably used N-oxyl group is the 2,2,6,6-tetramethylpiperidine-N-oxyl radical. Examples of such N-oxyls likewise to be used according to the invention are to be found in WO 69/17002. Examples of syntheses of the aminocompounds on which the N-oxyls are based are also mentioned in this publication.

Further N-oxyl radicals suitable according to the invention are the N-oxyl radicals stated in DE-19651307, as part of the mixture disclosed there. This publication is hereby incorporated in its entirety.

Preferred nitroxyl compounds are the following:
1-oxyl-2,2,6,6-tetramethylpiperidine,
1-oxyl-2,2,6,6-tetramethylpiperidin-4-ol,
1-oxyl-2,2,6,6-tetramethylpiperidin-4-one,
1-oxyl-2,2,6,6-tetramethylpiperidin-4-yl acetate,
1-oxyl-2,2,6,6-tetramethylpiperidin-4-yl 2-ethylhexanoate,
1-oxyl-2,2,6,6-tetramethylpiperidin-4-yl stearate,
1-oxyl-2,2,6,6-tetramethylpiperidin-4-yl benzoate,
1-oxyl-2,2,6,6-tetramethylpiperidin-4-yl (4-tert-butyl) benzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
N,N'-bis(1-oxyl-2,2,6,6-tetramethylpiperidin-4-yl) adipamide,
N-(1-oxyl-2,2,6,6-tetramethylpiperidin-4-yl)caprolactam,
N-(1-oxyl-2,2,6,6-tetramethylpiperidin-4-yl) dodecylsuccinimide,
2,4,6-tris[N-butyl-N-(1-oxyl-2,2,6,6,-tetramethylpiperidin-4-yl]-s-triazine,
N,N'-bis(1-oxyl-2,2,6,6-tetramethylpiperidin-4-yl)-N,N'-bisformyl-1,6-diaminohexane,
4,4'-ethylenebis(1-oxyl-2,2,6,6-tetramethylpiperazin-3-one) and
tris(2,2,6,6-tetramethyl-1-oxyl-piperidin-4-yl) phosphite.

The N-oxyl radicals used according to the invention can be prepared by various synthesis steps known per se. A preferred method of preparation makes use of the oxidation of secondary amine, whose NH group is oxidized to the corresponding N-oxyl group. Suitable oxidizing agents are peroxides, such as H$_2$O$_2$, tert-butyl hydroperoxide, cumyl hydroperoxide, peracids, such as metachloroperbenzoic acid, α-chloroperbenzoic acid, paracetic acid, paranitroperbenzoic acid or perbenzoic acid, or magnesium monoperoxyphthalate. The oxidation can be carried out in an inert solvent, such as CH$_2$Cl$_2$, petroleum ether, toluene, xylene or benzene.

The parent secondary amines are either known from the literature or can be readily prepared by a person skilled in the art of organic chemical synthesis by modifying processes known per se. DE 19651307 discloses the preparation of various N-oxyl radicals suitable according to the invention.

The stabilizer system can be added as such or in the form of a solution as solvent, such as water, $C_1$–$C_6$-alkanols, such as methanol, ethanol, propanol, n-butanol, isobutanol and tert-butanol, if required as a mixture with water, ketones, such as acetone, methyl ethyl ketone, methyl propyl ketone or methyl butyl ketone, diols such as glycol or propylene glycol, and their alkyl mono- and diethers, oligomeric or polymeric ethylene glycols and propylene glycols and their alkyl ethers, diamines, such as ethylenediamine or propylenediamine and their alkyl mono- or diiminoethers, oligomeric or polymeric ethylenediamines and their alkyl iminoethers. Preferably, however, the mixture to be stabilized is used in the form of a solvent or suspending medium for the stabilizer system. Thus, the mixture obtained in the dehydrogenation of ethylbenzene and predominantly comprising styrene, ethylbenzene, toluene and further substituted aromatics can be used for this purpose.

An important application of the invention is the isolation of ethylenically unsaturated compounds from a corresponding crude mixture by distillation, for example the isolation of styrene from crude styrene by distillation. Below, the invention is illustrated with reference to the isolation of styrene from crude styrene, but is not restricted thereto. Unless otherwise evident from the context, all statements apply correspondingly to other ethylenically unsaturated compounds and mixtures containing them.

A typical arrangement for the industrial distillation of styrene is described in Kunststoff-Handbuch, Volume 4 (Polystyrol), Section 2.3.1.4, 30 et seq. (Munich 1996).

Because the boiling points of styrene and ethylbenzene are close together (145 and 136° C., respectively, at atmospheric pressure) and the purity of the styrene has to meet high requirements, this purification requires an expensive distillation procedure. Purification is effected as a rule by distillation in a cascade comprising a plurality of distillation columns, the bottom discharge of one distillation column being fed in each case into the downstream distillation column. The number of successive columns is denoted below by n. The feed is preferably effected in each case in the region of the middle of the column. In the first column, the styrene-containing mixture is introduced as feed. The parameter n is a positive integer $\geq 2$ and indicates the number of distillation columns in the cascade. In general, it is preferable if n is from 2 to 4, e.g. 2 or 3. As a rule, pure styrene is taken off via the top in the n th distillation column while the components of the crude styrene which have a lower boiling point than that of styrene are taken off via the top in the distillation columns upstream of the n th column. The bottom discharge of the n th column can be fed to a concentrator, for example a thin-film evaporator or flash evaporator, for isolating residual amounts of styrene and/or methylstyrenes. The low boiler fraction obtained can be further separated in a working-up column. The arrangement and connection of the individual distillation columns for carrying out the novel process can be readily determined by a person skilled in the art, on the basis of his technical judgment. An apparatus for obtaining the electronic signal is provided at a suitable point, for example in at least one column bottom or pipeline.

In the first distillation column, the styrene-containing mixture is introduced as feed. In a suitable embodiment of the invention, an apparatus for online ESR measurement is provided in the bottom of at least one downstream column or in the pipeline via which the bottom discharge is passed into the next column. The stabilizer system is preferably introduced into at least one distillation column upstream of the n th distillation column, for example into the first distillation column. The stabilizer system can expediently be mixed with the feed of a distillation column or added to the bottom of the column. The addition of the stabilizer system is controlled, according to the invention, by comparing the electronic signal, which correlates with the concentration of the N-oxyl radicals in the crude styrene column, with a reference value which is chosen so that it corresponds to an N-oxyl radical concentration of, for example, 1–1000 ppm.

The N-oxyl radicals and the optional components of the stabilizer system are sparingly volatile compounds. A high boiler fraction which contains the stabilizer system therefore accumulates in the bottom of the n th distillation column.

In a preferred embodiment, a part-stream of the solution of the stabilizer system which collects in the bottom of the n th distillation column is recycled to the high boiler fraction and is added to the feed of at least one distillation column upstream of the n th distillation column. The recycled stream can be divided up and fed in at a plurality of points, for example to the feed of the first and to the feed of the second column. Expediently, the recycled stabilizer solution is mixed with the feed of an upstream distillation column; however, the recycled solution can also be added directly to the bottom of an upstream distillation column.

As a rule, it is preferable if the high boiler fraction removed from the bottom of the n th distillation column is concentrated before recycling or discharge, i.e. is freed from low boilers. For example, apparatuses such as a thin-film evaporator or flash evaporator are suitable for this purpose. The low boiler fraction obtained can be further separated in a working-up column into styrene and α- or β-methylstyrene. After the concentration, the concentration of the N-oxyl radicals in the high boiler fraction is in general from 0.2 to 100 g/l.

The N-oxyl radicals are preferably used in an amount such that the concentration of the N-oxyl radicals in the bottom of each distillation column is at least 0.1 ppm, in particular from 1 to 500 ppm, preferably from 5 to 150 ppm. The amount in the bottom of a distillation column is composed of any recycled amount and freshly added amount of N-oxyl radicals. The novel process is particularly advantageous if some of the high boiler fraction is recycled because it permits optimum utilization of the active N-oxyl radicals contained in the recycled portion. The metering of fresh stabilizer system is controlled in such a way that only the difference between recycled amount of N-oxyl radicals and specified effective concentration is added. Larger excess amounts, which for safety reasons are unavoidable in processes to date because the N-oxyl radical concentration was not accurately known, are not required in the novel process.

The N-oxyl radicals used according to the invention are effective inhibitors for styrene polymerization and greatly suppress the formation of styrene polymers during the distillation. In the bottom of the n th distillation column, there is as a rule a higher temperature than in the bottoms of the upstream columns since fractions having a lower boiling point than that of styrene are distilled off in the upstream columns while styrene is taken off via the top in the n th column. It is assumed that partial reactivation of the N-oxyl radicals takes place in the bottom of the n th distillation column. The reactivation can be illustrated by the following equation:

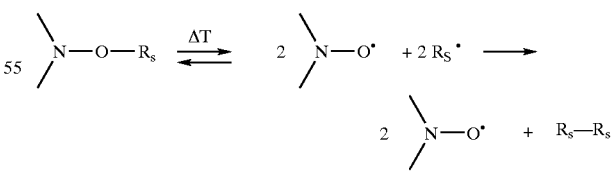

where $R_S$ is an organic radical comprising one or more styrene radicals. The bonding of the $R_S$ radical to the oxygen atom of the nitroxyl radical is reversible at elevated temperatures. When the temperature is increased, a steady-state concentration of free $R_S$ radicals is present in an equilibrium reaction, and said radicals can combine in pairs, the nitroxyl radicals being liberated again.

The number of cycles Z during which on average the N-oxyl radicals pass through the (n–1) th distillation column can be defined as a measure of the recycling of N-oxyl radicals which are contained in the recycled stream of the high boiler fraction. The number of cycles Z is related by the following equation to the portion x of recycled high boiler fraction, based on the total amount of high boiler fraction which is obtained in the bottom of the n th distillation column:

$$Z = \frac{1}{1-x}$$

Preferably, the N-oxyl radicals pass through the (n–1) th distillation column on average at least 1.4, preferably 2.0, in particular 2.5, particularly preferably 3, times. In general, amounts of more than 0.3, preferably more than 0.5, in particular more than 0.6, and particularly preferably more than 0.67, of the recycled stabilizer solution correspond to said numbers of cycles. In general, it is preferable to recycle from 10 to 90, preferably from 30 to 85, in particular from 50 to 80, % by weight of the high boiler fraction obtained in the bottom of the n th distillation column.

It has been found that particularly good reactivation of the recycled stabilizer solution can be achieved if the part-stream is heated to more than 130° C. prior to recycling. In a preferred embodiment of the novel process, the part-stream of the solution of the stabilizer system is heated to more than 130° C., in particular 135–160° C., prior to recycling. The heating can expediently be carried out over a period of from 1 to 300, preferably from 10 to 60, minutes.

According to a further preferred embodiment of the novel process, the part-stream of the solution of the stabilizer system is treated with oxygen prior to recycling. The treatment with oxygen can be carried out at from 20 to 200° C., preferably from 50 to 170° C., in particular from 100 to 150° C. The treatment with oxygen can advantageously be carried out using an oxygen-containing gas mixture, in particular a gas mixture comprising essentially oxygen and nitrogen, the oxygen content of said gas mixture being from 3 to 10% by volume. A suitable oxygen-containing gas mixture is, for example, clean air. The treatment can be effected at atmospheric or superatmospheric pressure. The treatment with oxygen leads to an effective regeneration of free N-oxyl radicals.

All apparatuses which permit a liquid, in particular viscous liquid, to be brought into contact with a gas are essential for carrying out the oxygen treatment, for example apparatuses for pumping a gas through a liquid, for forcing a gas stream into a liquid stream, etc. Suitable mixing containers, for example stirred mixing containers, may also be provided.

In a preferred embodiment of the novel process, the stabilizer system furthermore contains at least one polymerization retardant. Polymerization retardants are defined as substances which do not completely inhibit a free radical polymerization of the styrene monomers but reduce the polymerization rate. The combination of the N-oxyl radicals to be used according to the invention with at least one polymerization retardant has the advantage that, for example in the case of an operating fault when the concentration of N-oxyl radicals falls below a threshold value required for effective inhibition, polymerization of the amount of monomers present in the system does not start abruptly. Rather, there is a slow increase in the oligomer or polymer content, so that, if required, countermeasures can be taken. The combination of the N-oxyl radicals with a polymerization retardant furthermore has a synergistic effect. This is because the different action mechanisms supplement one another, and with the same total concentration of the stabilizer system, the greater polymerization-inhibiting effect is achieved with the use or combination of N-oxyl radicals with a polymerization retardant than with the isolated use of N-oxyl radicals or polymerization retardants. Preferably, the polymerization retardant is used in an amount of from 50 to 2000 ppm, based on styrene. The weight ratio of N-oxyl radicals to polymerization retardant is preferably from 1:20 to 20:1.

Particularly suitable polymerization retardants are aromatic nitrocompounds, in particular of the formula III

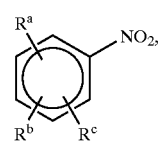

(III)

where $R^a$, $R^b$ and $R^c$, independently of one another, are each hydrogen, $C_1$–$C_6$-alkyl, halogen or a radical of the formula CN, SCN, NCO, OH, $NO_2$, COOH, CHO, $SO_2H$ or $SO_3H$, it being possible for the aromatic ring to be benzofused.

Suitable compounds are, for example, 1,3-dinitrobenzene, 1,4-dinitrobenzene, 2,6-dinitro-4-methylphenol, 2-nitro-4-methylphenol, 2,4,6-trinitrophenol, 2,4-dinitro-1-naphthol, 2,4-dinitro-6-methylphenol, 2,4-dinitrochlorobenzene, 2,4-dinitrophenol, 2,4-dinitro-6-sec-butylphenol, 4-cyano-2-nitrophenol or 3-iodo-4-cyano-5-nitrophenol. Aromatic nitrocompounds, such as 2,6-dinitro-4-methylphenol, 2-nitro-4-methylphenol, 2,4-dinitro-6-sec-butylphenol or 2,4-dinitro-6-methylphenol, are preferably used.

The stabilizer system in the novel process can, if required, also contain one or more costabilizers from the group consisting of the aromatic nitroso compounds, phenothiazines, quinones, hydroquinones and their ethers, phenols and their ethers, hydroxylamines and phenylenediamines.

Further costabilizers may also be substituted phenols or hydroquinones, for example the following: 4-tert-butylpyrocatechol, methoxyhydroquinone, 2,6-di-tert-butyl-4-methylphenol, n-octadecyl-β-(3,5-di-tert-butyl-4-hydroxyphenyl)propionate, 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, 1,3,5-tris(3,5-di-tert-butyl-4-hydroxybenzyl) isocyanurate, 1,3,5-tris[β-(3,5-di-tert-butyl-4-hydroxyphenyl)propionyloxyethyl] isocyanurate, 1,3,5-tris(2,6-dimethyl-3-hydroxy-4-tert-butylbenzyl) isocyanurate or pentaerythrityl tetrakis[β-(3,5-di-tert-butyl-4-hydroxyphenyl)propionate].

In a preferred embodiment of the novel process, the stabilizer system furthermore contains an activator in addition to the N-oxyl radicals used according to the invention. An activator is defined as a chemical compound which is capable of increasing the activity of the N-oxyl radicals by catalyzing, for example, free radical combination reactions.

Preferably, the activator is used in an amount of from 0.01 to 20% by weight, based on the N-oxyl radicals.

Suitable activators are in particular iron compounds or other transition metal compounds, in particular those which can exist in different valency states.

Preferred iron compounds suitable as activators are selected from the group consisting of the a) iron carbonyls and carbonyl ferrates,
b) organometallic iron carbonyl compounds,
c) unsubstituted and substituted ferrocene compounds,
d) iron compounds having ligands which contain oxygen, nitrogen, sulfur or phosphorus as donor atoms, alone or as a mixture,
e) iron halide and iron pseudohalide compounds.

Group a) includes, for example, compounds such as iron pentacarbonyl, $Fe(CO)_5$, diiron nonacarbonyl, $Fe_2(CO)_9$, triiron dodecacarbonyl, $Fe_3(Co)_{12}$, or hexairon octadecacarbonyl, $Fe_6(CO)_{18}$, all of which are soluble in slightly polar or nonpolar media. The carbonyl ferrates, such as $M_2Fe(CO)_4$, $M_2Fe_2(CO)_8$ and $M_2Fe_3(CO)_{11}$, where M is one equivalent of an alkali metal or alkaline earth metal, may also be mentioned here. The corresponding Na compounds are preferably used.

Organometallic iron carbonyl compounds of group b) are, for example, compounds of the formula

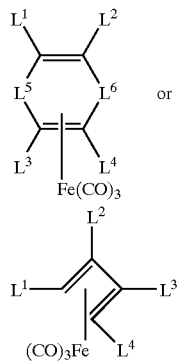

where
$L^1$–$L^4$ are each hydrogen or $C_1$–$C_4$-alkyl, such as methyl, ethyl, propyl or tert-butyl
$L^5$, $L^6$ are each —$(CH_2)_n$— or —CO—, where, for $L^5$ and $L^6$, n independently of one another are 0, 1, 2 or 3.
Examples of suitable compounds are

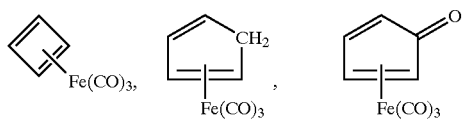

Compounds of group c) which are to be used according to the invention include ferrocene itself and the derivatives substituted on one or both cyclopentadienyl rings. Dimeric ferrocene derivatives may also be used.

For example, complexes or salts of Fe(II)/Fe(III) with O-containing ligands, such as sulfate, acetate, oxalate, citrate, tartrate, lactate, gluconate or acetylacetonate (acac), may be used as compounds of group d).

However, further exclusively or predominantly O-containing ligands for Fe(II) or Fe(III) may also be cyclic polyethers, such as spherands, cryptands, cryptaspherands, hemispherands, coronands or open-chain ethers of this group and podands.

It is also possible to use complexes with N-containing chelate ligands, such as ethylenediamine (en), 1,10-phenanthroline (phen), 1,8-naphthpyridine (napy), 2,2'-bipyridine (pipy) and dibenzo[b,i]-1,4,8,11-tetraaza-(14) annulene (taa), as well as complexes of iron with various, substituted porphyrin ligands, as known from the literature (for example, B. Mennier, Chem. Rev. 92 (8) (1992), 1411–1456). Other N-containing ligands are phthalocyanine and derivatives thereof.

N,O-containing ligands, such as ethylenediaminetetraacetic acid (EDTA) and nitrilotriacetic acid (NTA), result in compounds such as
[Fe(EDTA)(H$_2$O)]$^{\ominus/2\ominus}$, [Fe(NTA)(H$_2$O)$_2$] and [Fe(NTA)(H$_2$O)$_2$]$^{\ominus}$, respectively,
and 8-hydroxyquinoline (quin) and 5-methyl-8-hydroxyquinoline (H$_3$C-quin) result in compounds such as
[Fe(quin)$_3$]/[Fe(quin)$_3$]$^{2\ominus}$ and
[Fe(H$_3$C-quin)$_3$]/[Fe(H$_3$C-quin)$_3$]$^{2\ominus}$, respectively,
which can likewise be used.

Further Fe compounds to be used according to the invention are Fe complexes with Schiff's bases of salicylaldehydes.

The preparation of these N,O-containing ligands is known and is carried out as a rule by condensation of aromatic or heteroaromatic α-hydroxyaldehyde with an aliphatic or aromatic diamine or polyamine. Thereafter, the reaction of the ligands with an Fe salt is carried out in aqueous solution.

Other Fe compounds which have S-containing ligands and may be used are, for example,

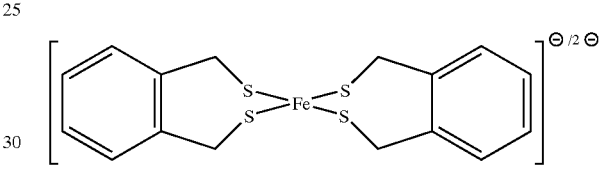

or [Fe$_4$S$_4$(SR)$_4$]$^{4\ominus/3\ominus}$, as well as complexes of Fe(II)/Fe(III) with dithiocarbonates $R_2NCS_2^{\ominus}$ such as [Fe(S$_2$CNR$_2$)$_3$]$^{\ominus}$ (R=CH$_3$, C$_2$H$_5$).

It is also possible to use compounds of group e). Among the iron halides, the Fe(II) and Fe(III) salts of Cl and Br and the complexes FeX$_4^{\ominus/2\ominus}$ (X=Cl, Br) are preferably used. The iron pseudohalide compounds to be used according to the invention include, for example, [Fe(CN)$_6$]$^{3\ominus}$/[Fe(CN)$_6$]$^{4\ominus}$ and thiocyanate complexes of the series [Fe(SCN)$^{3-x}$(H$_2$O)$_{3+x}$]$^{x\oplus}$ (x=0, 1 or 2).

Opposite ions preferably used for all negatively charged complex ions mentioned are H$^{\oplus}$, Na$^{\oplus}$, K$^{\oplus}$ and ammonium ions NH$_4^{\ominus}$ and N(CH$_3$)$_4^{\ominus}$, but, for the hexacyanoferrates, in addition to K$^{\oplus}$, also Fe$^{2\oplus}$ in the case of [Fe(CN)$_6$]$^{3\ominus}$ and Fe$^{3\oplus}$ in the case of [Fe(CN)$_6$]$^{4\ominus}$.

In the case of the positively charged complex ions mentioned, Cl$^{\ominus}$, Br$^{\ominus}$, I$^{\ominus}$, SO$_4^{2\ominus}$, H$_3$CCO$_2^{\ominus}$, CrO$_4^{2\ominus}$, BF$_4^{\ominus}$ and B(C$_6$H$_5$)$_4^{\ominus}$ are preferably used as opposite ions.

The example which follows illustrates the invention.

In a distillation unit according to FIG. 1, crude styrene which originates from the dehydrogenation of ethylbenzene is continously distilled.

The distillation unit used consists of a benzene (toluene) column 1, to which a mixture comprising, for example, essentially styrene, ethylbenzene, benzene and toluene 1a is fed, an ethylbenzene column 2, which serves for separating off and recovering the ethylbenzene 2a, and the styrene column 3, from which the pure styrene 3a is finally obtained. Ethylbenzene column 2 and styrene column 3 are each provided with reboilers 2b and 3b, respectively, i.e. they have a heatable bottom.

The bottom discharge of column 3 is fed to the setup comprising essentially apparatuses 4 and 5. 4 is a concentrator which is in the form of a thin-film evaporator or flash evaporator and in which the product stream removed from the column bottom a is freed from low boilers. The low boilers are further separated in a working-up column (not shown) into styrene and α-(β-)methylstyrene. A part-stream of the concentrate obtained from 4 and temporarily stored in 5 is recycled to the feed of column 1 and/or 2.

Bottom discharge from the ethylbenzene column 2 is passed, via the T-distributor 7a and the directional valve 7b, periodically through the integrated ESR measuring cell 7 (magnet and alternating field source are not shown). The signal detected in the measuring cell 7 is fed via a signal converter a to a comparator 9 with a selectable reference value. The reference value is chosen so that it corresponds to an N-oxyl radical concentration of about 200 ppm, based on crude styrene. The comparator 9 controls the addition of a solution of the stabilizer system via the metering valve 6a, said solution being stored in the storage container 6. The stabilizer system used contains 1-oxyl-2,2,6,6-tetramethylpiperidin-4-ol (hydroxy-TEMPO).

We claim:

1. A process for preventing undesired polymerization, comprising:
    maintaining an effective concentration of a stabilizer which comprises N-oxyl radicals in a mixture containing ethylenically unsaturated compounds, wherein
    (i) an electronic signal which correlates with the concentration of the N-oxyl radicals in the mixture is obtained periodically or continuously,
    (ii) the electronic signal is compared with a reference value, and
    (iii) addition of a stabilizer to the mixture is controlled according to the comparison (ii).

2. The process as claimed in claim 1, wherein the electronic signal is obtained by exposing the mixture or a portion thereof to a magnetic field and simultaneously applying an alternating electromagnetic field, the resonance caused by the N-oxyl radicals being detected.

3. The process as claimed in claim 1, wherein the concentration of the N-oxyl radicals in the mixture ranges from 5 to 150 ppm, based on ethylenically unsaturated compounds.

4. The process as claimed in claim 1, wherein the stabilizer contains a polymerization retardant.

5. The process as claimed in claim 4, wherein the polymerization retardant is an aromatic nitro compound.

6. The process as claimed in claim 1, wherein the ethylenically unsaturated compound is a vinylaromatic compound.

7. The process as claimed in claim 1, wherein the reference value is dependent on at least one other measured variable which is selected from the group consisting of temperature, redox potential, near infrared transmission or absorption, turbidity, viscosity, density or refractive index of the mixture.

8. The process as claimed in claim 1, wherein the said N-oxyl radicals are present in the mixture in an amount of at least 0.1 ppm.

9. The process as claimed in claim 1, wherein the ethylenically unsaturated compounds are selected from the group consisting of α,β-ethylenically unsaturated $C_3$–$C_6$-monocarboxylic acids or $C_4$–$C_6$-dicarboxylic acids, esters of α,β-ethylenically unsaturated $C_3$–$C_6$-monocarboxylic acids or $C_4$–$C_6$-dicarboxylic acids, vinylaromatic compounds, heteroaromatic vinyl compounds, vinyl esters of $C_1$–$C_{18}$-monocarboxylic acids or dicarboxylic acids, linear or branched 1-olefins or cyclic olefins, acrylonitrile, methacrylonitrile, vinyl and allyl $C_1$–$C_{40}$-alkyl ethers, acrylamide, alkyl-substituted acrylamides, vinyl halides, vinylidene halides, polyethylenically unsaturated compounds, sulfo-containing monomers, $C_1$–$C_4$-hydroxyalkyl esters of ethylenically unsaturated $C_3$–$C_6$-monocarboxylic acids or $C_4$–$C_6$-dicarboxylic acids, vinylphosphonic acid compounds, alkylaminoalkyl (meth)acrylates or alkylaminoalkyl (meth)acrylamides or their quaternization products, allyl esters of $C_1$–$C_{30}$-monocarboxylic acids, N-vinyl compounds, diallyldimethylammonium chloride, acrolein, methacrolein, monomers containing 1,3-diketo groups, monomers containing urea groups, silyl-containing monomers and glycidyl-containing monomers.

10. The process as claimed in claim 1, wherein the stabilizer containing N-oxyl radicals is selected from the group consisting of 1-oxyl-2,2,6,6-tetramethylpiperidine, 1-oxyl-2,2,6,6-tetramethylpiperidin-4-ol, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl-2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl (4-tert-butyl)benzoate, bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl) sebacate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, N,N'-bis(1-oxyl-2,2,6,6-tetramethylpiperidin-4-yl) adipamide, N-(1-oxyl-2,2,6,6-tetramethylpiperidin-4-yl) caprolactam, N(1-oxyl-2,2,6,6-tetramethylpiperidin-4-yl) dodecylsuccinimide, 2,4,6-tris[N-butyl-N-(1-oxyl-2,2,6,6-tetramethylpiperidin-4-yl)-s-triazine, N,N'-bis(1-oxyl-2,2,6,6 tetramethylpiperidin-4-yl)-N,N'-bis-formyl-1,6-diaminohexane, 4,4'-ethylenebis(1-oxyl-2,2,6,6-tetramethylpiperazin-3-one) and tris(2,2,6,6-tetramethyl-1-oxyl-piperidin-4-yl) phosphite.

11. A process for isolating ethylenically unsaturated compounds, comprising:
    while distilling a mixture of ethylenically unsaturated compounds, maintaining an effective concentration of a stabilizer in the mixture which comprises free N-oxyl radicals, wherein
    (i) an electronic signal which correlates with the concentration of the N-oxylradicals in the mixture is obtained periodically or continuously,
    (ii) the electronic signal is compared with a reference value, and
    (iii) addition of a stabilizer to the mixture is controlled according to the comparison (ii).

12. The process as claimed in claim 11, wherein the electronic signal is obtained by exposing the mixture or a portion thereof to a magnetic field and simultaneously applying an alternating electromagnetic field, the resonance caused by the N-oxyl radicals being detected.

13. The process as claimed in claim 11, wherein the distillation is conducted in a cascade of at least two distillation columns, in which a high boiler fraction containing the stabilizer accumulates in the bottom of at least one distillation column and a stream of a portion of the high boiler fraction is removed and is mixed with a feed that enters an upstream column.

14. The process as claimed in claim 11, wherein the reference value is dependent on at least one other measured variable which is selected from the group consisting of temperature, redox potential, near infrared transmission or absorption, turbidity, viscosity, density or refractive index of the mixture.

15. The process as claimed in claim 11, wherein the said N-oxyl radicals are present in the mixture in an amount of at least 0.1 ppm.

16. The process as claimed in claim 11, wherein the ethylenically unsaturated compounds are selected from the group consisting of α,β-ethylenically unsaturated $C_3$–$C_6$-monocarboxylic acids or $C_4$–$C_6$-dicarboxylic acids, esters of α,β-ethylenically unsaturated $C_3$–$C_6$-monocarboxylic acids or $C_4$–$C_6$-dicarboxylic acids, vinylaromatic compounds, heteroaromatic vinyl compounds, vinyl esters of $C_1$–$C_{18}$-monocarboxylic acids or dicarboxylic acids, linear or branched 1-olefins or cyclic olefins, acrylonitrile, methacrylonitrile, vinyl and allyl $C_1$–$C_{40}$-alkyl ethers, acrylamide, alkyl-substituted acrylamides, vinyl halides, vinylidene halides, polyethylenically unsaturated compounds, sulfo-containing monomers, $C_1$–$C_4$-hydroxyalkyl esters of ethylenically unsaturated $C_3$–$C_6$-monocarboxylic acids or $C_4$–$C_6$-dicarboxylic acids, vinylphosphonic acid compounds, alkylaminoalkyl (meth) acrylates or alkylaminoalkyl (meth)acrylamides or their quaternization products, allyl esters of $C_1$–$C_{30}$-monocarboxylic acids, N-vinyl compounds, diallyldimethylammonium chloride, acrolein, methacrolein, monomers containing 1,3-diketo groups, monomers containing urea groups, silyl-containing monomers and glycidyl-containing monomers.

17. The process as claimed in claim 11, wherein the stabilizer containing N-oxyl radicals is selected from the group consisting of 1-oxyl-2,2,6,6-tetramethylpiperidine, 1-oxyl-2,2,6,6-tetramethylpiperidin-4-ol, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl (4-tert-butyl)benzoate, bis(1-oxyl-2,2,6,6-tetramethylpiperidin-4-yl) succinate, bis(oxyl-2,2,6,6-tetramethylpiperidin-4-yl) adipate, bis(1-oxyl-2,2,6,6-tetramethylpiperidin-4-yl) sebacate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, N,N'-bis(1-oxyl-2,2,6,6-tetramethylpiperidin-4-yl) adipamide, N-(1-oxyl-2,2,6,6-tetramethylpiperidin-4-yl) caprolactam, N-(1-oxyl-2,2,6,6-tetramethylpiperidin-4-yl) dodecylsuccinimide, 2,4,6-tris[N-butyl-N-(1-oxyl-2,2,6,6-tetramethylpiperidin-4-yl)-s-triazine, N,N'-bis(1-oxyl-2,2,6,6-tetramethylpiperidin-4-yl)-N,N'-bis-formyl-1,6-diaminohexane, 4,4'-ethylenebis(1-oxyl-2,2,6,6-tetramethylpiperazin-3-one) and tris(2,2,6,6-tetramethyl-1-oxyl-piperidin-4-yl) phosphite.

18. The process as claimed in claim 11, wherein the concentration of the N-oxyl radicals in the mixture ranges from 5 to 150 ppm, based on ethylenically unsaturated compounds.

19. The process as claimed in claim 11, wherein the stabilizer contains a polymerization retardant.

20. The process as claimed in claim 19, wherein the polymerization retardant is an aromatic nitro compound.

21. The process as claimed in claim 11, wherein the ethylenically unsaturated compound is a vinylaromatic compound.

* * * * *